United States Patent
Small, Jr.

(10) Patent No.: US 12,011,498 B2
(45) Date of Patent: Jun. 18, 2024

(54) COMPOSITIONS AND METHODS FOR PREVENTING AND REVERSING ASPECTS OF AGING

(71) Applicant: CENTERS FOR AGE CONTROL, INC., Las Vegas, NV (US)

(72) Inventor: Elliott C. Small, Jr., Las Vegas, NV (US)

(*) Notice: Subject to any disclaimer, the term of this patent is extended or adjusted under 35 U.S.C. 154(b) by 0 days.

(21) Appl. No.: 17/745,190

(22) Filed: May 16, 2022

(65) Prior Publication Data

US 2022/0273539 A1    Sep. 1, 2022

Related U.S. Application Data

(63) Continuation of application No. 16/634,765, filed as application No. PCT/US2018/043920 on Jul. 26, 2018, now Pat. No. 11,364,187.

(60) Provisional application No. 62/538,574, filed on Jul. 28, 2017.

(51) Int. Cl.
| A61K 8/49 | (2006.01) |
| A61K 8/34 | (2006.01) |
| A61K 8/36 | (2006.01) |
| A61K 8/42 | (2006.01) |
| A61K 8/92 | (2006.01) |
| A61Q 19/00 | (2006.01) |
| A61Q 19/08 | (2006.01) |

(52) U.S. Cl.
CPC ............ *A61K 8/4926* (2013.01); *A61K 8/342* (2013.01); *A61K 8/347* (2013.01); *A61K 8/361* (2013.01); *A61K 8/42* (2013.01); *A61K 8/922* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| 1,001,603 | A | 8/1911 | Aschauer |
| 5,939,082 | A | 8/1999 | Oblong et al. |
| 8,446,061 | B2 | 5/2013 | Nakayama et al. |
| 8,747,915 | B1 | 6/2014 | Giampapa |
| 9,913,793 | B2 | 3/2018 | Perricone |
| 9,913,797 | B2 | 3/2018 | Dueva-Koganov |
| 2011/0274680 | A1 | 11/2011 | Mazed et al. |
| 2016/0250241 | A1 | 9/2016 | Deren-Lewis et al. |
| 2018/0221397 | A1* | 8/2018 | Duronio .................. A61K 31/09 |

FOREIGN PATENT DOCUMENTS

| CN | 106860065 A | 6/2017 |
| CN | 106860182 A | 6/2017 |
| FR | 2759292 A1 * | 8/1998 | ............ A61K 31/192 |
| WO | 2001043705 A2 | 6/2001 |
| WO | 2015066382 A1 | 5/2015 |
| WO | 2016149277 A1 | 9/2016 |
| WO | 2016200447 A1 | 12/2016 |
| WO | 2018039207 A1 | 3/2018 |
| WO | 2019023471 A1 | 1/2019 |

OTHER PUBLICATIONS

Drug Topics (Overview of pharmaceutical excipients used in tablets and capsules, Oct. 24, 2008). (Year: 2008).*
Australian Patent Office, International Search Report and Written Opinion for PCT/US2018-043920 dated Nov. 1, 2018, 15 pp.
Becam, et al. "Antibacterial activity of ceramide and ceramide analogs against pathogenic Neisseria" https://www.nature.com/articles/s41598-017-18071-w, published Dec. 15, 2017.
Bogan, et al. "Nicotinic Acid, Nicotinamide, and Nicotinamide Riboside: A Molecular Evaluation of NAD + Precursor Vitamins in Human Nutrition", Annu Rev. Nutr. 208, 28-115-30, first published online as a Review om Advance on Apr. 22, 2008.
Cherney, Kristeen, "Everything you should Know about Niacinamide" available online Aug. 29, 2018 (2018).
Van Hoogevest, et al. "The use of natural and synthetic phospholipids as pharmaceutical excipients" Eur Lipid Sci Technol. Sep. 2014; 116(9): 1088-1107, Published online Aug. 25, 2014, www.ncbi.nlm.nih.gov/pmc/articles/PMC4207189/.
Fu, et al. "A randomized, controlled comparative study of the wrinkle reduction benefits of a cosmetic niacinamide/peptide/retinyl propionate product regimen vs. a prescription 0.02% tretinoin product regimen" Br J Dermatol. Mar. 2010; 162(3): 647-654, www.ncbi.nlm.nih.gov/pmc/articles/PMC2841824/.
Gomes, et al. "Declining NAD+ Induces a Pseudohypoxic State Disrupting Nuclear-Mitochondrial Communication during Aging" Article| vol. 155, Issue 7, p. 1624-1638, Dec. 19, 2013 www.cell.com/abstract/S0092-8674(13)01521-3.
Green, et al. "Nicotinamide restores cognition in Alzheimer's disease transgenic mice via a mechanism involving sirtuin inhibition and selective reduction of Thr231-phosphotau" www.alzforum.org/papers/nicotinamide-restores-cognition-alzheimers-disease-transgenic-mice-mechanism-involving#/show-more, Nov. 5;28(45):11500-10. PubMed.
Hirobe, Tomohisha "Keratinocytes regulate the function of melanocytes" www.sciencedirect.com/science/article/pii/S1027811714000238, Elsevier, Dermatologica Sinica 32 (2014) 200-204.
Huebner, et al. "Age Effects on Internal Anal Sphincter Thickness and Diameter in Nulliparous Females" https://www.ncbi.nlm.nih.gov/pmc/articles/PMC2288793/, Dis Colon Rectum. Sep. 2007; 50(9): 1405-1411.

(Continued)

*Primary Examiner* — Melissa S Mercier
(74) *Attorney, Agent, or Firm* — Daniel J. Chalker; Edwin S. Flores; Chalker Flores, LLP

(57) ABSTRACT

The present invention includes compositions and methods preventing or reversing the symptoms of aging in a subject in need thereof comprising administering to the subject an amount of a composition comprising pterostilbene, nicotinamide, and optionally vitamin A (retinol), and one or more retinoids effective to prevent or reverse the symptoms of aging.

18 Claims, No Drawings

(56) References Cited

OTHER PUBLICATIONS

McCormak, et al. "A Review of Pterostilbene Antioxidant Activity and Disease Modification" Hindawai Publishing corporation, Oxidative Mdicine and Cellular Longevity, vol. 2013, Article ID 575482, 15 pp.

Mukherjee, et al. "Retinoids in the treatment of skin aging: an overview of clinical efficacy and safety" Published online Dec. 2006, Clin Interv Aging. Dec. 2006; 1(4): 327-348, www.ncbi.nlm.nih.gov/pmc/articles/PMC2699641.

Sirerol, et al. "Topical treatment with pterostilbene, a natural phytoalexin, effectively protects hairless mice against JVB radiation-induced skin damage and carcinogenesis" Apr. 2015 Free Radical Biology and Medicine 85, Elsevier, available online Apr. 4, 2015, Free Radical Biology and Medicine 85 (2015) 1-11.

Schallreuter, et al. "Basic evidence for epidermal H2O2/ONOO-mediated oxidation/nitration in segmental vitiligo is supported by repigmentation of skin and eyelashes after reduction of epidermal H2O2 with topical NB-UVB-activated pseudocatalase PC-KUS" The FASEB Journal, first published Apr. 29, 2013, www.fasebj.org/content/27/8/3113.full?SID=6f4a5e87-0ced-4b10-b1f9-30118dd9e176.

\* cited by examiner

COMPOSITIONS AND METHODS FOR PREVENTING AND REVERSING ASPECTS OF AGING

CROSS REFERENCE TO RELATED APPLICATIONS

This application claims priority to, and is a continuation patent application of U.S. patent application Ser. No. 16/634,765 filed on Jan. 28, 2020, which is the National Phase of International Application No. PCT/US2018/043920, filed on Jul. 26, 2018, which claims the benefit under 35 U.S.C. § 119(e) of U.S. Provisional Application No. 62/538,574, filed Jul. 28, 2017. All of which are hereby incorporated by reference in their entirety.

TECHNICAL FIELD OF THE INVENTION

The present invention relates in general to the field of compositions and methods for preventing and reversing aspects of aging that include pterostilbene, nicotinamide, vitamin A (retinol), other retinoids, and in certain aspect, Tretinoin, Ceramide 3, Ceramide 6-II, and Ceramide 1, Sphingolipids; and orally taking wheat (*Triticum vulgare*) oil extract, glycolipids, phytoceramides, and/or glycosylceramides.

BACKGROUND OF THE INVENTION

Without limiting the scope of the invention, its background is described in connection with the treatment and prevention of aging.

One such composition and method is taught in U.S. Pat. No. 9,913,797, issued to Dueva-Koganov, et al., entitled, "Bioactive compositions having hair anti aging activity". These inventors are said to teach bioactive composition and method of using the composition is provided having anti-aging, antioxidant and/or free radical scavenging properties that includes an effective amount of a bioactive blend selected from: a first composition comprising a combination of a camellia serum fraction and a feverfew serum fraction in a weight ratio of about 10:90 to about 90:10; and/or a second composition comprising a combination of a parsley serum fraction and a kelp serum fraction in a weight ratio of about 10:90 to about 90:10; and optionally a dermatologically acceptable carrier.

Another such composition and method is taught in U.S. Pat. No. 9,913,793, issued to Perricone entitled, "Treatment of skin, including aging skin, to improve appearance." This inventor is said to teach a composition for topical or transdermal delivery, treatment of skin, and improving the appearance of skin, e.g., medically or cosmetically that includes nitric oxide and/or peptides such as thyrotropin-releasing hormone (TRH) and/or GnRH (gonadotropin-releasing hormone). The nitric oxide and/or peptide may be present within a first phase comprising a lecithin, such as phosphatidylcholine, in the form or liposomes, micelles, or other structures containing nitric oxide, peptides, or both. The composition can take the form of a gel, a cream, a lotion, an ointment, a solution, a solid "stick," etc., that can be rubbed or sprayed onto the skin. Other aspects of the present invention are generally directed to methods of making or using such compositions, methods of promoting such compositions, kits including such compositions, or the like.

However, despite these improvements, a need remains for effective formulations for use in preventing or reducing the symptoms of aging.

SUMMARY OF THE INVENTION

In one embodiment, the present invention includes a method of preventing or reversing the symptoms of aging in a subject in need thereof comprising administering to the subject an amount of a composition comprising pterostilbene and nicotinamide effective to prevent or reverse the symptoms of aging. In one aspect, the composition further comprises vitamin A (retinol), and one or more retinoids. In another aspect, the composition further comprises one or more retinoids selected from at least one of retinyl palmitate, retinyl retinoate, retinyl proprionate, or tretinoin. In another aspect, each of the pterostilbene and nicotinamide are provided in an amount that is synergistic for at least one of preventing or reversing symptoms of aging. In another aspect, the method further comprises adding one or more pharmaceutically acceptable excipients. In another aspect, the composition comprises: 100 to 500 mg Nicotinamide, e.g., 125, 150, 175, 200, 225, 250, 275, 300, 325, 350, 375, 400, 425, 450, or 475 to 500 mg. In another aspect, the composition comprises: 50 to 500 mg Pterostilbene, e.g., 75, 100, 125, 150, 175, 200, 225, 250, 275, 300, 325, 350, 375, 400, 425, 450, or 475 to 500 mg. In another aspect, the composition comprises: 125 to 2,000 mg Nicotinamide (Niacinamide) and 50 to 1,000 mg Pterostilbene. In another aspect, the method further comprises applying topically a composition of: 0.05% weight to volume Tretinoin with Ceramide 3, Ceramide 6-II, and Ceramide 1, Sphingolipids; and orally taking wheat (*Triticum vulgare*) oil extract, glycolipids, phytoceramides, or glycosylceramides, in an amount sufficient to reduce wrinkles. In another aspect, the composition further comprises at least one of a chelating agent, a skin soothing agent, a skin conditioning agent, a humectant, a moisturizing agent, a nutrient, a thickener, or an In another aspect, the composition comprises per dose: 0.5 to 2 grams Pterostilbene, and 1 to 5 grams Nicotinamide, per 100 milliliters of water. In another aspect, the composition further comprises one or more excipients selected from water, Sodium Phytate, Aloe Barbadensis Leaf Juice, Glycerin, *Pyrus malus* (Apple) Fruit Extract, Phenoxyethanol, Ethylhexylglycerin, Tocopherol, Caprylic/Capric Triglyceride, *Argania spinosa* Kernel Oil, Dipentaerythrityl Hexa C5-9 Acid Esters, Dimethicone, Acrylates/C10-30 Alkyl Acrylate Crosspolymer, Sodium Hydroxide, Hydroxyethyl Acrylate/Sodium Acryloyldimethyl Taurate Copolymer, Squalane, Polysorbate 60, or Sorbitan Isostearate. In another aspect, the range per dose of the composition is 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300 mg of the composition per 100 ml of water. In another aspect, the range per dose of the combined agents is 150, 175, 200, 225, 250, 275, 300, 75 to 300, 80 to 275, 90 to 250, 100 to 225, 125 to 200, 150 to 175 mg of the composition per dose. In another aspect, the range per dose of the combined agents is 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 mg per dose. In another aspect, the method further comprises adapting the composition to be administered topically, orally, prenatally, intravenously, intraperitoneally, intranasally, intrapulmonary, vaginal, transdermal, rectal, subcutaneously, intracutaneously, intraocular, or intramuscularly.

In another embodiment, the present invention includes a method of treating preventing or reversing the symptoms of aging in a subject comprising: identifying a subject having at least one of preventing or reversing the symptoms of aging; and providing the patient with a medical composition that comprises an amount of a composition comprising pterostilbene, nicotinamide, vitamin A (retinol), and one or more retinoids effective to prevent or reverse the symptoms of aging. In one aspect, the composition further comprises vitamin A (retinol), and one or more retinoids. In another aspect, the composition further comprises one or more retinoids selected from at least one of retinyl palmitate, retinyl retinoate, retinyl proprionate, or tretinoin. In another aspect, each of the pterostilbene and nicotinamide are provided in an amount that is synergistic for at least one of preventing or reversing symptoms of aging. In another aspect, the method further comprises adding one or more pharmaceutically acceptable excipients. In another aspect, the composition comprises: 100 to 2,000 mg Nicotinamide, e.g., 125, 150, 175, 200, 225, 250, 275, 300, 325, 350, 375, 400, 425, 450, or 475 to 500 mg. In another aspect, the composition comprises: 50 to 1,000 mg Pterostilbene, e.g., 75, 100, 125, 150, 175, 200, 225, 250, 275, 300, 325, 350, 375, 400, 425, 450, or 475 to 500 mg. In another aspect, the composition comprises: 125 to 2,000 mg Nicotinamide (Niacinamide) and 50 to 1,000 mg Pterostilbene. In another aspect, the method further comprises applying topically a composition of: 0.05% weight to volume Tretinoin with Ceramide 3, Ceramide 6-II, and Ceramide 1, Sphingolipids; and orally taking wheat (*Triticum vulgare*) oil extract, glycolipids, phytoceramides, or glycosylceramides, in an amount sufficient to reduce wrinkles. In another aspect, the composition further comprises at least one of a chelating agent, a skin soothing agent, a skin conditioning agent, a humectant, a moisturizing agent, a nutrient, a thickener, or an emollient. In another aspect, the composition comprises per dose: 0.5 to 2 grams Pterostilbene, and 1 to 5 grams Nicotinamide, per 100 milliliters of water. In another aspect, the composition further comprises one or more excipients selected from water, Sodium Phytate, Aloe Barbadensis Leaf Juice, Glycerin, *Pyrus malus* (Apple) Fruit Extract, Phenoxyethanol, Ethylhexylglycerin, Tocopherol, Caprylic/Capric Triglyceride, *Argania spinosa* Kernel Oil, Dipentaerythrityl Hexa C5-9 Acid Esters, Dimethicone, Acrylates/C10-30 Alkyl Acrylate Crosspolymer, Sodium Hydroxide, Hydroxyethyl Acrylate/Sodium Acryloyldimethyl Taurate Copolymer, Squalane, Polysorbate 60, or Sorbitan Isostearate. In another aspect, the range per dose of the composition is 150, 200, 250, 270, 300, 350, 400, 450, 500, 540, 600, 700, 750, 800, 900, 1,000, 1,100, 1,200, 1,300, 1,400, 1,500, 1,600, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300 mg of the composition per 100 ml of water. In another aspect, the range per dose of the combined agents is 150, 175, 200, 225, 250, 275, 300, 75 to 300, 80 to 275, 90 to 250, 100 to 225, 125 to 200, 150 to 175 mg of the composition per dose. In another aspect, the range per dose of the combined agents is 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 mg per dose. In another aspect, the method further comprises adapting the composition to be administered topically, orally, prenatally, intravenously, intraperitoneally, intranasally, intrapulmonary, vaginal, transdermal, rectal, subcutaneously, intracutaneously, intraocular, or intramuscularly. In another aspect, the method further comprises adding one or more agents selected from Tretinoin, Ceramide 3, Ceramide 6-II, Ceramide 1, Sphingolipids, wheat (*Triticum vulgare*) oil extract, glycolipids, phytoceramides, or glycosylceramides.

In another embodiment, the present invention includes a composition comprising pterostilbene and nicotinamide. In one aspect, the composition further comprises vitamin A (retinol), and one or more retinoids. In another aspect, the composition further comprises one or more retinoids selected from at least one of retinyl palmitate, retinaldehyde, retinyl retinoate, retinyl proprionate, or tretinoin. In another aspect, each of the pterostilbene and nicotinamide are provided in an amount that is synergistic for at least one of preventing or reversing symptoms of aging. In another aspect, the composition further comprises one or more pharmaceutically acceptable excipients. In another aspect, the composition comprises: 100 to 2,000 mg Nicotinamide, e.g., 125, 150, 175, 200, 225, 250, 275, 300, 325, 350, 375, 400, 425, 450, or 475 to 500 mg. In another aspect, the composition comprises: 50 to 1,000 mg Pterostilbene, e.g., 75, 100, 125, 150, 175, 200, 225, 250, 275, 300, 325, 350, 375, 400, 425, 450, or 475 to 500 mg. In another aspect, the composition comprises: 125 to 2,000 mg Nicotinamide (Niacinamide) and 50 to 1,000 mg Pterostilbene. In another aspect, the composition is adapted for topical administration and includes: 0.05% weight to volume Tretinoin with Ceramide 3, Ceramide 6-II, and Ceramide 1, and/or Sphingolipids; and orally taking wheat (*Triticum vulgare*) oil extract, glycolipids, phytoceramides, or glycosylceramides, in an amount sufficient to reduce wrinkles. In another aspect, the composition further comprises at least one of a chelating agent, a skin soothing agent, a skin conditioning agent, a humectant, a moisturizing agent, a nutrient, a thickener, or an In another aspect, the composition comprises per dose: 0.5 to 2 grams Pterostilbene, and 1 to 5 grams Nicotinamide, per 100 milliliters of water. In another aspect, the composition further comprises one or more excipients selected from water, Sodium Phytate, Aloe Barbadensis Leaf Juice, Glycerin, *Pyrus malus* (Apple) Fruit Extract, Phenoxyethanol, Ethylhexylglycerin, Tocopherol, Caprylic/Capric Triglyceride, *Argania spinosa* Kernel Oil, Dipentaerythrityl Hexa C5-9 Acid Esters, Dimethicone, Acrylates/C10-30 Alkyl Acrylate Crosspolymer, Sodium Hydroxide, Hydroxyethyl Acrylate/Sodium Acryloyldimethyl Taurate Copolymer, Squalane, Polysorbate 60, or Sorbitan Isostearate. In another aspect, the range per dose of the composition is 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300 mg of the composition per 100 ml of water. In another aspect, the range per dose of the combined agents is 150, 175, 200, 225, 250, 275, 300, 75 to 300, 80 to 275, 90 to 250, 100 to 225, 125 to 200, 150 to 175 mg of the composition per dose. In another aspect, the range per dose of the combined agents is 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 mg per dose. In another aspect, the composition is adapted to be administered topically, orally, prenatally, intravenously, intraperitoneally, intranasally, intrapulmonary, vaginal, transdermal, rectal, subcutaneously, intracutaneously, intraocular, or intramuscularly. In another aspect, the composition further comprises one or more agents selected from Tretinoin, Ceramide 3, Ceramide 6-II, Ceramide 1, Sphingolipids, wheat (*Triticum vulgare*) oil extract, glycolipids, phytoceramides, or glycosylceramides.

In yet another embodiment, the present invention includes a composition consisting essentially of pterostilbene, nicotinamide, vitamin A (retinol), and one or more retinoids. In one aspect, the composition further comprises one or more agents selected from Tretinoin, Ceramide 3, Ceramide 6-II, Ceramide 1, Sphingolipids, wheat (*Triticum vulgare*) oil extract, glycolipids, phytoceramides, or glycosylceramides.

In yet another embodiment, the present invention includes a composition consisting of pterostilbene, nicotinamide, vitamin A (retinol), and retinoids, wherein the retinoids are selected from at least one of retinyl palmitate, retinaldehyde, retinyl retinoate, retinyl proprionate, or tretinoin. In one aspect, the composition further comprises one or more agents selected from Tretinoin, Ceramide 3, Ceramide 6-II, Ceramide 1, Sphingolipids, wheat (*Triticum vulgare*) oil extract, glycolipids, phytoceramides, or glycosylceramides.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. N/A—not applicable.

The present inventor has recognized a need to treat and prevent the symptoms of aging. A composition of pterostilbene, nicotinamide, vitamin A (retinol), and one or more retinoids have been used to prevent or reduce the symptoms of aging. It is not intuitive or obvious that such compounds could be used effectively to prevent or reduce the symptoms of aging alone or in combination with the other agents, as taught herein. Among other treatments, as taught herein, the present invention relates to compositions and methods for topical or transdermal delivery, treatment of skin, and improving the appearance of skin, e.g., medically or cosmetically.

According to one aspect of the present invention, a composition as described herein is used to treat skin. In one embodiment of the invention, transdermal (topical) application of pterostilbene, nicotinamide, vitamin A (retinol), and one or more retinoids prevents or reduces the symptoms of aging.

A dosage unit for use of the composition of the present invention may be a single compound or mixtures thereof with other compounds. The compounds may be mixed together, form ionic or even covalent bonds. The composition of the present invention may be administered in oral, intravenous (bolus or infusion), intraperitoneal, subcutaneous, transdermal, transcutaneous, intrapulmonary, intranasal, suppositories, or intramuscular form, including prenatally, all using dosage forms well known to those of ordinary skill in the pharmaceutical arts. As such, the composition that includes: pterostilbene, nicotinamide, vitamin A (retinol), and one or more retinoids may be adapted for any location for administration. Depending on the particular location or method of delivery, different dosage forms, e.g., tablets, capsules, pills, powders, granules, liquids, elixirs, tinctures, suspensions, syrups, and emulsions may be used to provide the composition of the present invention to a patient in need of therapy for a medical condition or symptom. The composition may also be administered as any one of known salt forms.

In one aspect, the composition comprises: 100 to 2,000 mg Nicotinamide, e.g., 125, 150, 175, 200, 225, 250, 275, 300, 325, 350, 375, 400, 425, 450, or 475 to 500 mg. In another aspect, the composition comprises: 50 to 1,000 mg Pterostilbene, e.g., 75, 100, 125, 150, 175, 200, 225, 250, 275, 300, 325, 350, 375, 400, 425, 450, or 475 to 500 mg. In another aspect, the composition comprises: 125 to 2,000 mg Nicotinamide (Niacinamide) and 50 to 1,000 mg Pterostilbene. In another aspect, the composition is adapted for topical administration and includes: 0.05% weight to volume Tretinoin with Ceramide 3, Ceramide 6-II, and Ceramide 1, and/or Sphingolipids; and orally taking wheat (*Triticum vulgare*) oil extract, glycolipids, phytoceramides, or glycosylceramides, in an amount sufficient to reduce wrinkles. In another aspect, the composition further comprises at least one of a chelating agent, a skin soothing agent, a skin conditioning agent, a humectant, a moisturizing agent, a nutrient, a thickener, or an emollient. In another aspect, the composition comprises per dose: 0.5 to 2 grams Pterostilbene, and 1 to 5 grams Nicotinamide, per 100 milliliters of water. In another aspect, the composition further comprises one or more excipients selected from water, Sodium Phytate, Aloe Barbadensis Leaf Juice, Glycerin, *Pyrus malus* (Apple) Fruit Extract, Phenoxyethanol, Ethylhexylglycerin, Tocopherol, Caprylic/Capric Triglyceride, *Argania spinosa* Kernel Oil, Dipentaerythrityl Hexa C5-9 Acid Esters, Dimethicone, Acrylates/C10-30 Alkyl Acrylate Crosspolymer, Sodium Hydroxide, Hydroxyethyl Acrylate/Sodium Acryloyldimethyl Taurate Copolymer, Squalane, Polysorbate 60, or Sorbitan Isostearate. In another aspect, the range per dose of the composition is 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300 mg of the composition per 100 ml of water. In another aspect, the range per dose of the combined agents is 150, 175, 200, 225, 250, 275, 300, 75 to 300, 80 to 275, 90 to 250, 100 to 225, 125 to 200, 150 to 175 mg of the composition per dose. In another aspect, the range per dose of the combined agents is 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 mg per dose. The composition may be adapted to be administered topically, orally, prenatally, intravenously, intraperitoneally, intranasally, intrapulmonary, vaginal, transdermal, rectal, subcutaneously, intracutaneously, intraocular, or intramuscularly. In another aspect, the composition further comprises one or more agents selected from Tretinoin, Ceramide 3, Ceramide 6-II, Ceramide 1, Sphingolipids, wheat (*Triticum vulgare*) oil extract, glycolipids, phytoceramides, or glycosylceramides.

The composition of the present invention is typically administered in a mixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the composition may be formulated to provide, e.g., maximum and/or consistent dosing for the particular form for oral, vaginal, rectal, topical, transdermal, subcutaneous, intravenous injection or parenteral administration. While the composition may be administered alone, it will generally be provided in a stable salt form mixed with a pharmaceutically acceptable carrier. The carrier may be solid or liquid, depending on the type and/or location of administration selected.

For example, the composition may be included in a tablet or capsule. Tablets or capsules may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with an non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

The composition may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

The composition may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the composition may be coupled one or more biodegradable polymers to achieve controlled release of the composition, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the composition and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water-soluble salt of the active ingredient, suitable stabilizing agents, and if necessary, buffering salts. Antioxidizing agents such as sodium bisulfate, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propylparaben, and/or chlorobutanol. Suitable pharmaceutical carriers are described in Remington's Pharmaceutical Sciences, Mack Publishing Company, a standard reference text in this field, relevant portions incorporated herein by reference.

For direct delivery to the nasal passages, sinuses, mouth, throat, esophagus, trachea, lungs and alveoli, the composition may also be delivered as an intranasal form via use of a suitable intranasal vehicle. For dermal and transdermal delivery, the composition may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of composition may include the following forms.

Capsules. Capsules may be prepared by filling standard two-piece hard gelatin capsules each with pterostilbene, nicotinamide, vitamin A (retinol), and one or more retinoids. The capsules may also contain one or more agents selected from Ceramide 3, Ceramide 6-II, and Ceramide 1, wheat (*Triticum vulgare*), oil extract containing glycolipids, phytoceramides, and/or glycosylceramides.

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 100-500 milligrams of the active ingredient. The capsules are washed and dried.

Tablets. A large number of tablets are prepared by conventional procedures so that the dosage unit was 100-500 milligrams of active ingredient (pterostilbene, nicotinamide, vitamin A (retinol), and one or more retinoids), 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption. The capsules may also contain one or more agents selected from Ceramide 3, Ceramide 6-II, and Ceramide 1, wheat (*Triticum vulgare*), oil extract containing glycolipids, phytoceramides, and/or glycosylceramides.

Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration. In addition to the pterostilbene, nicotinamide, the injectable solution may also contain one or more agents selected from vitamin A (retinol), and one or more retinoids, Ceramide 3, Ceramide 6-II, and Ceramide 1, wheat (*Triticum vulgare*), oil extract containing glycolipids, phytoceramides, and/or glycosylceramides.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

For rectal and vaginal routes of administration, the composition of the present invention can be formulated as solutions, retention enemas, suppositories or ointments containing conventional suppository bases such as cocoa butter or other glycerides. Suppositories may also include about 0.5% to about 50% of a compound of the invention, disposed in a polyethylene glycol (PEG) carrier, for example, PEG 1000 (96%) and PEG 4000 (4%).

An exemplary transdermal device generally includes a reservoir defined by an impermeable backing layer and a membrane. The backing layer and the membrane are joined together about the outer periphery of the device. These layers may be joined by an adhesive, a heat seal, or the like. The transdermal device may also include an adhesive layer to attach the device to the skin of a subject. A release liner will generally cover the adhesive that the user removes prior to use of the device to expose adhesive layer.

Backing layer defines the distal side of the patch, that is, the side furthest from the skin in use. The backing layer functions as the primary structural element of the device and provides the device with its mechanical properties, e.g., flexibility. The backing layer serves as a protective, impermeable covering to prevent loss of the particles containing the active compound(s) in the reservoir. Suitable backing materials include commercially available films for medical use, such as those supplied by 3M corporation, Dow Chemical or Fasson Medical Industries. Typical backing materials are made from polyester or the like and may be pigmented or metallized.

The reservoir is defined generally by the space or gap between the backing layer and the membrane, provides a storage structure in which to retain the suspension of particles containing the active compound(s) to be administered. One side of the reservoir is generally defined by a highly porous member that retains the formulation within the reservoir, i.e., it deters bulk flow of the formulation out of the reservoir, but allows passage of the formulation from the reservoir into the skin. Materials suitable for use as membrane include non-woven fabrics such as nonwoven polyesters, polyethylene, polypropylene and other synthetic polymers. The material is heat or otherwise sealable to the backing layer to provide a barrier to transverse flow of reservoir contents.

An adhesive layer allows for the device to be affixed to the skin. This layer is made from a pharmaceutically acceptable pressure sensitive adhesive, such as polydimethylsiloxane, polyisobutylene, polyacrylate, polyurethane and the like. It will be appreciated that the adhesive layer can also be a peripheral, or rim, adhesive layer.

The transdermal device containing the particles containing active compound(s) may also include a peel strip or release liner to cover the surface of the adhesive layer and to prevent loss of reservoir contents during storage. Prior to use, the release liner is removed from the device. The release liner is typically a material impermeable to the reservoir contents, for example polyethylene terephthalate, and is releasable usually by treatment with a silicone or fluorocarbon.

Transdermal devices generally include a backing layer, a membrane and a peripheral adhesive layer. The backing layer and membrane may be glued or heat-sealed about the periphery of the device. A reservoir defined by the space between the backing layer and the membrane provides for storage of particles containing the active compound(s) to be administered transdermally. The peripheral adhesive layer may be applied directly to backing layer. A release liner protects the device during storage.

The contents of the reservoir may even be in direct contact with the skin when the device is affixed to a subject. The reservoir in this device is composed of an absorbent sponge or a porous, highly permeable polymer. Materials suitable for the reservoir include polyurethane, polyethylene or polypropylene materials. An impermeable backing layer prevents loss of reservoir contents through the distal, top side of the device. The backing layer is coated on its distal side with an adhesive overlay, which is protected by a backing or polymer layer. Prior to use, the peripheral edge of the adhesive overlay is exposed by peeling a release liner and an impermeable protective strip from the proximal, skin side of the device. The transdermal delivery device may be adhesively attached to the skin of the user, although other methods for attaching the device to the skin are contemplated and suitable, e.g., an elastic arm band or an adjustable belt.

Transdermal device membranes are generally porous, highly permeable membranes with minimal resistance to diffusion of the reservoir contents, relative to the skin. At the same time, the membrane functions to prevent bulk flow of the particles containing the active compound(s) in the reservoir. Materials suitable for use as a membrane include hydrophilic and hydrophobic fabrics, cloths and polymer films having a porosity suitable for retaining the particles containing the active compound(s). Such materials may be nonwoven or woven, yet having a defined pore size. It will be appreciated that the membrane can be selected to provide more or less diffusional resistance as desired. For example, to design a device where the membrane is rate controlling, rather than the skin, a membrane with a tighter weave or smaller pore size can be selected.

For topical administration, the composition can be incorporated into creams, ointments, gels, transdermal patches and the like, as disclosed herein. The composition can also be incorporated into medical dressings, for example wound dressings e.g. woven (e.g. fabric) dressings or non-woven dressings (e.g. gels or dressings with a gel component). The use of polymers in dressings is known, and such dressings, or indeed any dressings, may further incorporate the oligomers of the invention. In addition to the pterostilbene, nicotinamide, the topical formulation may also contain one or more agents selected from vitamin A (retinol), and one or more retinoids, Ceramide 3, Ceramide 6-II, and Ceramide 1, wheat (*Triticum vulgare*), oil extract containing glycolipids, phytoceramides, and/or glycosylceramides.

Disclosed herein are combinations of pterostilbene, nicotinamide (a form of vitamin B3), vitamin A (retinol), and other retinoids: retinyl palmitate, retinaldehyde, retinyl retinoate, retinyl proprionate, tretinoin, and others, and other ingredients and methods for preventing and reversing the decline in the health and appearance of humans and other mammals due to aging or other causes. The ingredient combinations provided herein can be used for the production of nutritional supplements, pharmaceutical compositions and medicaments that are orally, nasally, and topically consumed or injected. Some or all of these modes of consumption can be done simultaneously.

Example 1. Nutritional Supplement for General Aging Reversal

Synergy of ingredient combination. The present invention includes a composition with a combination of pterostilbene and nicotinamide. Claims will include all effects of the nicotinamide and pterostilbene combination and effects from the combination of nicotinamide, pterostilbene. Included among these effects but not limited to them are reversal of gray hair, more youthful muscle tissue, more youthful body tissues in general, better brain function, more energy, reduction of skin wrinkles, better sleep, improvement of erectile dysfunction, etc.

A study by Dr. David Sinclair at Harvard Medical School saw 60 year old human equivalent mice with muscle tissue resembling 20 years old after just one week of increased NAD levels caused by injections of nicotinamide mono nucleotide (NMN). (cell.com/abstract/50092-8674(13) 01521-3). The present inventor shows herein that Resveratrol and pterostilbene have a surprising synergistic effect when used in the claimed amounts. Pterostilbene, also known as Resveratrol Dimethyl Ether, is absorbed about four times more effectively in the human body—about 80% absorption for pterostilbene versus about 20% for resveratrol. Therefore, it is considered to be a superior successor to reseratrol.

Pterostilbene is also known to protect against UVB radiation and cancer: researchgate.net/publication/274642935_Topical_treatment_with_pterostilbene_a_natural_phytoalexin_effectively_protects_hairless_mice_against_UVB_radiation-induced_skin_damage_and_carcinogenesis:

Case Study. A combination of nicotinamide and pterostilbene was provided daily. Each morning, the subject's muscles felt a sensation similar to having completed a workout on weight machines at the gym, even when he had not been to the gym. It was like a "workout in a bottle." The subject then began applying the combination nasally, and topically. After about 30 days, the subject began to notice that the graying of his hair had begun to reverse after he began using the pterostilbene/nicotinamide combination both orally, nasally, and topically on all parts of his body (generally, at locations where there is hair). The hair in his nostrils became mostly black instead of mostly white. Within 60 days, the edge of his hair on the left front side of his head went from about half gray to mostly black. Within 90 days, the hair on my lower abdomen went from speckled gray to mostly black. In addition, the mustache showed a decline gray hair. The composition further caused increased hair growth on head, arms and most of the subject's body.

NMN converts to NAD in a one step metabolic pathway. Tryptophan (TRP), nicotinic acid (NA), nicotinamide (NAM), and nicotinamide riboside (NR) can be taken orally and also are utilized through distinct metabolic pathways to form NAD. (researchgate.net/publication/5422539_Nicotinic_Acid_Nicotinamide_and_Nicotinamide_Riboside_A_Molecular_Evaluation_of_NAD_Precursor_Vitamins_in_Human_Nutrition).

Tryptophan requires 8 steps. Nicotinic Acid requires 3 steps. Nicotinamide requires two steps, converting to Nicotinamide mononucleotide (NMN), which is subsequently converted to NAD. Nicotinamide riboside converts in both a 2-step and a 3-step pathway, converting to NMN to NAD or converting to Nicotinamide to NMN to NAD.

Although Nicotinamide converts the fastest on average, nicotinamide riboside is widely preferred because it activates the sirtuin 1 longevity gene in any concentration level while nicotinamide is believed to activate the sirtuin 1 longevity gene at low concentrations and inhibit it at high concentrations.

However, Dr. Sinclair states in a comment on another study, "One must be careful when calling nicotinamide an "inhibitor" in this experiment. While it is true that Dr. Sinclair's lab showed that nicotinamide is a direct inhibitor of SIRT1 enzyme in vitro, it is also a precursor of NAD+, and NAD+ is a co-substrate (i.e., activator) of SIRT1. In vivo, there is an abundant enzyme called Nampt in cells and serum that initiates the conversion of nicotinamide to NAD+. Therefore it is possible, but not a limitation of the present invention, that nicotinamide is activating SIRT1 in vivo, not inhibiting it. This would fit with other papers showing that SIRT1 is neuroprotective." (alzforum.org/papers/nicotinamide-restores-cognition-alzheimers-disease-transgenic-mice-mechanism-involving#show-more).

There could be clues to the above in this study: journals.plosorg/plosbiology/article?id=10.1371/journal.pbio.1001603. The authors state, "We were surprised to find that inhibiting SIRT1 with nicotinamide did not prevent the resveratrol-induced increase in mitochondrial proteins . . . ."

Numerous clinical studies have shown that topically applied nicotinamide reduces the wrinkles and dark spots on skin. This 2015 report lists such reports in its section on niacinamide, which is another name for nicotinamide: ncbi.nlm.nih.gov/pmc/articles/PMC4587894/. Here is another example: dermatologytimes.modernmedicine.com/dermatology-times/news/anti-aging-effects-niacin-amide?page=0%2C2. These age reversal effects could also be evidence that nicotinamide is activating the sirtuin 1 gene in vivo as suggested by Dr. Sinclair.

Thus, nicotinamide could be a better choice than nicotinamide riboside. Also, Nicotinamide typically has a retail cost of about 9 cents per gram compared to about 6 dollars per gram for nicotinamide riboside. Resveratrol and pterostilbene both have a retail cost of about 2 dollars per gram, but 1 gram of pterostilbene is equivalent to 4 grams of resveratrol.

It was also found herein, there is additional synergy in the combination of pterostilbene with nicotinamide because pterostilbene also activates the sirtuin one enzyme, thereby preventing the possibility that nicotinamide might offset its numerous benefits by inhibiting the sirtuin one enzyme in high concentrations.

Example 2. Topical Treatment to Reduce Graying Hair

A specific process to reverse gray hair should have more success when it is also part a general process that reverses aging. Thereby, other processes upon which that process depends can occur. This invention claims the combination of all or any selections from pterostilbene, nicotinamide, retinaldehyde or any of other retinoids, and phospholipid based emulsifiers/system formers and others. There are no topically applied products on the market containing pterostilbene.

The level of naturally occurring hydrogen peroxide in cells is controlled by the enzyme catalase that converts hydrogen peroxide into to water and oxygen. (See pdb101.rcsb.org/motm/57) Graying hair is caused when levels of catalase decline below levels required to prevent hydrogen peroxide from bleaching the pigment. (See fasebj.org/content/27/8/3113.full?sid=6f4a5e87-0ced-4b10-b1f9-30118dd9e176 and sciencedirect.com/science/article/pii/S1027811714000238). Numerous companies offer oral supplements containing catalase, but none has been proven to work reliably. There appears to be no research that proves that catalase survives the digestive system.

By way of explanation, and in no way a limitation of the present invention, Pterostilbene may reverses the effects of aging in many ways. Among them, Pterostilbene increases the production of catalase. Topically and orally administered pterostilbene is a far more effective way to increase catalase levels in the skin and hair. Emulsifiers/System formers such as phospholipid based ones that are more biocompatible generally facilitate a higher than normal penetration of active ingredients such as topically applied pterostilbene. (See ncbi.nlm.nih.gov/pmc/articles/PMC4207189/). Pterostilbene UV protection is especially useful for hair bearing skin, for which sun blocker application is not desirable for cosmetic reasons.

See researchgate.net/publication/274642935_Topical_treatment_with_pterostilbene_a_natural_phytoalexin_effectively_protects_hairless_mice_against_UVB_radiation-induced_skin_damage_and_carcinogenesis.

Nicotinamide converts to nicotinamide adenine dinucleotide (NAD) in the cells of humans and other mammals, reversing the age related decline of the level of NAD. NAD facilitates communication between a cell nucleus and the energy producing mitochondria in the cell. Improved general cellular function provides an optimal environment for fulfillment of the effects of other ingredients in the combination. See pubs.sciepub.com/ajssm/3/5/3/.

Retinaldehyde is the strongest of the non-prescription forms of vitamin A (retinoids) for rejuvenating aged or photodamaged skin. In the skin, retinaldehyde converts to retinoic acid (tretinoin) in one step. The other non-prescription retinoids require multiple steps to convert. Tretinoin is only available by prescription and is the molecular form of vitamin A that actually provides the skin benefits such as increased collagen, cellular growth and differentiation, cell surface alterations, and immune modulation. This improved skin condition provides an optimal environment for fulfillment of the effects of other ingredients in the combination. See ncbi.nlm.nih.gov/pmc/articles/PMC2699641/. Phospholipid based emulsifiers/system formers and others facilitate a higher than normal penetration of the active ingredients.

The present composition can also include one or more agents selected from Ceramide 3, Ceramide 6-II, Ceramide 1, Sphingolipids, glycolipids, phytoceramides, and/or glycosylceramides. Thus, the present invention encompasses the ceramides category broadly, including sphingolipids, such as a sphingoid base sphingosine as well as short-chain C6 and long-chain C16-ceramides, and azido-functionalized ceramide analogs.

Example 3. Topical Treatment to Reduce Wrinkles in Skin

A specific process to reduce skin wrinkles should have more success when it is also part a general process that reverses aging. Thereby, other processes upon which that process depends can occur. This invention claims the combination of all or any selections from pterostilbene, nicotinamide, retinaldehyde or any of other retinoids, and phospholipid based emulsifiers/system formers and others. There are no topically applied products on the market containing pterostilbene.

Tretinoin, also known as Retin-A and retinoic acid, is generally considered to be the most effective treatment for reducing wrinkles. See ncbi.nlm.nih.gov/pubmed/

17441463. Tretinoin is available only by prescription. This invention claims a non-prescription combination of ingredients that can work to reduce wrinkles with a level of effectiveness similar to tretinoin.

A study accomplished similar results with nicotinamide, peptides, and retinyl propionate versus 0.02% tretinoin. See ncbi.nlm.nih.gov/pmc/articles/PMC2841824/. This invention uses pterostilbene as well as nicotinamide, peptides, retinaldehyde. Phospholipid based emulsifiers/system formers or others are added to facilitate a higher than normal penetration of the active ingredients. Pterostilbene reverses effects of aging in many ways. (See https://examine.com/supplements/pterostilbene/.) That provides an environment that facilitates the effectiveness of the other ingredients.

Retinoids make skin more sensitive to Ultraviolet radiation. Therefore, they are usually used at night. The UV protective ability of pterostilbene can make possible the use of retinoids in daytime without the need for a sunblocker. See researchgate.net/publication/274642935_Topical_treatment_with_pterostilbene_a_natural_phytoalexin_effectively_protects_hairless_mice_against_UVB_radiation-induced_skin_damage_and_carcinogenesis.

Topically applying Ceramide 3, Ceramide 6-II, Ceramide 1 and/or Sphingolipids, overnight while also orally taking wheat (*Triticum vulgare*) oil extract containing glycolipids, phytoceramides, glycosylceramides provides further enhancement. nature.com/articles/s41598-017-18071-w.

Example 4. Topical and Oral Treatment to Dramatically Reduce Wrinkles Around Eyes Case Study. A subject was provided with a composition as taught herein for topical administration. The subject observed a dramatic reduction in wrinkles around his eyes after topically applying 0.05% Tretinoin with Ceramide 3, Ceramide 6-II, Ceramide 1 overnight while also orally taking wheat (*Triticum vulgare*) oil extract containing glycolipids, phytoceramides, glycosylceramides overnight. After just one night the crows feet on both eyes had disappeared and wrinkles under the eyes were significantly reduced. Combining with nicotinamide and pterostilbene enhances the effect by further activating the sirtuin 1 longevity enzyme that is activated pterostilbene and by NAD+ after conversion from nicotinamide.

Example 5. Topical Treatment to Protect Against Bacteria

Ceramides can protect against bacteria and cancerous cells: nature.com/articles/s41598-017-18071-w. Combining with nicotinamide and pterostilbene enhances the effect by further activating the sirtuin 1 longevity enzyme that is activated pterostilbene and by NAD+ after conversion from nicotinamide, thus protecting the subject against bacteria.

Example 6. Nutritional Supplement for Improvement of Bladder Control

Among other possibilities, the enhancement of muscle tissue by nicotinamide's conversion to NAD can help with bladder control to improve nocturia, the need to visit the bathroom multiple times at night, urinary incontinence, and other related conditions. See well.blogs.nytimes.com/2014/07/14/pelvic-exercises-for-men-too/. Combining nicotinamide with pterostilbene enhances the effect by further activating the sirtuin 1 longevity enzyme that is activated by NAD+.

Example 7. Nutritional Supplement for Improvement of Erectile Function

Among other possibilities, the enhancement of muscle tissue by nicotinamide's conversion to NAD can help erectile dysfunction. See medscape.com/viewarticle/761121 and well.blogs.nytimes.com/2014/07/14/pelvic-exercises-for-men-too/. Combining nicotinamide with pterostilbene enhances the effect by further activating the sirtuin 1 longevity enzyme that is activated by NAD+.

Example 8. Nutritional Supplement for Improvement of Bowel Function

Among other possibilities, the enhancement of muscle tissue by nicotinamide's conversion to NAD can help with anal sphincter control to improve bowel function, reducing the amount of toilet paper and/or wet wipes required as a person ages and returning bowel function to the natural and healthier inclination to have a bowel movement after every meal instead of less frequently, and help to prevent or stop fecal incontinence. ncbi.nlm.nih.gov/pmc/articles/PMC2288793/. Combining nicotinamide with pterostilbene enhances the effect by further activating the sirtuin 1 longevity enzyme that is activated by NAD+.

Lotion Formulation, 100 ml Bottle

|  | Benefits |
|---|---|
| Active Ingredients | |
| 0.5 to 2 grams Pterostilbene (also known as Resveratrol Dimethyl Ether) | antioxidant that fights against viral, bacterial, fungal attack and excessive sunlight |
| 1 to 5 grams Nicotinamide (also known as Niacinamide) | Vitamin B3 - improves skin barrier function, anti-aging, and moisturization |
| Other Ingredients | |
| Water/Aqua/Eau | |
| Sodium Phytate | Chelating agent |
| Aloe Barbadensis Leaf Juice | Skin soothing and conditioning |
| Glycerin | Humectant |
| Pyrus Malus (Apple) Fruit Extract, Glycerin | Extracted from dried apples, this moisturizing saccharide complex. Smoothes skin texture. |

| | Benefits |
|---|---|
| Niacinamide | Vitamin B3 - improves skin barrier function, anti-aging, and moisturization |
| Phenoxyethanol, Ethylhexylglycerin, Tocopherol | Wide spectrum preservative |
| Caprylic/Capric Triglyceride | skin emollient |
| Resveratrol Dimethyl Ether (also known as Pterostilbene) | antioxidant that fights against viral, bacterial, fungal attack and excessive sunlight |
| Argania Spinosa Kernel Oil | excellent nutritive properties that protect and lavish the skin with moisture without having an oily or greasy skin feel. This oil is rich with triterpenoids (skin healing properties), polyphenols (inflammation reduction), tocopherols (anti-aging activity) and two exclusive phytosterols (schottenol and spinasterol) that are ravenous free radical scavengers |
| Dipentaerythrityl Hexa C5-9 Acid Esters | non-greasy emollient imparts moisturization, cushion, and a unique sensory after feel |
| Dimethicone | Feel modifier that provides slip, cushion and a satin feel |
| Acrylates/C10-30 Alkyl Acrylate Crosspolymer | Emulsifier, stabilizer |
| Sodium Hydroxide Copolymer, Squalane, Polysorbate 60, Sorbitan Isostearate, Water/Aqua/Eau | pH adjuster/neutralizing agent |

Supplement Formulation
Active Ingredients:
  125 to 500 mg Nicotinamide (Niacinamide);
  50 to 500 mg Pterostilbene;
Inactive Ingredients:
  Microcrystalline Cellulose;
  Magnesium Stearate;
  Vegetarian capsule.

The composition may further comprise one or more of the following: vitamin A (retinol), and one or more retinoids, and/or one or more retinoids selected from at least one of retinyl palmitate, retinaldehyde, retinyl retinoate, retinyl proprionate, or tretinoin. The pterostilbene and nicotinamide are provided in an amount that is synergistic for at least one of preventing or reversing symptoms of aging. The composition may also include one or more pharmaceutically acceptable excipients. The composition may comprise: 125 to 500 mg Nicotinamide. The composition may comprise: 50 to 500 mg Pterostilbene. The composition may comprise: 125 to 500 mg Nicotinamide (Niacinamide) and 50 to 500 mg Pterostilbene. The composition may be adapted for topical administration into a composition of: 0.05% Tretinoin with Cerimide 3, Ceramide 6-II, and Ceramide 1; and orally taking wheat (*Triticum vulgare*) oil extract containing glycolipids, phytoceramides, glycosylceramides, in an amount sufficient to reduce wrinkles. The composition may also include one of a chelating agent, a skin soothing agent, a skin conditioning agent, a humectant, a moisturizing agent, a nutrient, a thickener, or an emollient. The composition may also include, per dose: 0.5 to 2 grams Pterostilbene, and 1 to 5 grams Nicotinamide, per 100 milliliters of water. The composition may also include one or more excipients selected from water, Sodium Phytate, Aloe Barbadensis Leaf Juice, Glycerin, *Pyrus malus* (Apple) Fruit Extract, Phenoxyethanol, Ethylhexylglycerin, Tocopherol, Caprylic/Capric *Argania spinosa* Kernel Oil, Dipentaerythrityl Hexa C5-9 Acid Esters, Dimethicone, Acrylates/C10-30 Alkyl Acrylate Crosspolymer, Sodium Hydroxide, Hydroxyethyl Acrylate/Sodium Acryloyldimethyl Taurate Copolymer, Squalane, Polysorbate 60, or Sorbitan Isostearate. The composition may also include a range per dose is 30, 40, 50, 60, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300 mg of the composition per 100 ml of water. The composition may also include a range per dose is 75, 80, 90, 100, 125, 150, 175, 200, 225, 250, 275, 300, 75 to 300, 80 to 275, 90 to 250, 100 to 225, 125 to 200, 150 to 175 mg of the composition per dose. The composition may also include a range per dose is 50, 75, 80, 90, 100, 125, 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 mg per dose. The composition may be adapted to be administered topically, orally, prenatally, intravenously, intraperitoneally, intranasally, intrapulmonary, vaginal, transdermal, rectal, subcutaneously, intracutaneously, intraocular, or intramuscularly.

The subjects in the treatment group indicated the following improvements in medical health, including: improved energy, much less fatigue and constipation, much calmer mood; huge increase in energy, increase in ability to concentrate; increased libido, bowel habits normalized, less fatigue and less dry mouth, no more constipation, calmer with less anxiety.

Pterostilbene-Nicotinamide Supplement can be much more effective if taken every few days instead of daily. Because both NAD+, converted in cells from Nicotinamide, and Pterostilbene both activate the Sirtuin 1 longevity enzyme, it appears that the effects of that activation last for more than one day. This has been observed up to 7 days.

Taking the supplement every day appears to dramatically limit the effects.

Having less than 8.5 to 9 hours of sleep each night appears to dramatically limit the effects. Just as teenagers require up to 9 hours of sleep for growth (according to WebMD), it appears that re-growing attributes degraded by aging requires 9 to 10 hours rather than the adult requirement of 7 to 8 hours of sleep.

These effects have been observed:
Deeper sleep.
More dreams.
Stronger erections.
Longer erections.
Larger ejaculation volume.
Reversal of dairy milk allergy that began at age 23 and steadily worsened with age.
Possible reversal of shrimp allergy that began around age 37.
Reversal of loose bowel movements to firm bowel movements.
Reversal of weaker anal muscles resulting in nearly all of the time having no need for use of wet wipes versus previous degradation requiring use of wet wipes nearly all of the time.
More energy.
Muscles feeling like they were exercised with weights at gym when they were not.
Skin less dry.
Eyes tearing more and return of "sand" around the eyes some nights.
Sweating more under arms and between legs.
Time appears to pass much more slowly, as it did during childhood.
More sensation in extremities: feet, ankles, hands, wrists.
The sclera (whites of the eyes) have become whiter.
Effects combined with nightly application of tretinoin (generic Retin-A) and oral supplement.
More rapid improvement after stopping application of any lotion to skin day or night and rinsing skin day and night only with water:
Deep eye crow's feet wrinkles have disappeared, even when smiling.
Dramatic reduction of wrinkles under eyes, even when smiling.
Dramatic reduction of nasojugal grooves (tear troughs under eyes).
Nearly eliminated glabellar lines (known as 11 lines or vertical frown lines between eyebrows).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of reducing or reversing gray in hair of a subject in need thereof comprising:
    applying topically to and taking orally and nasally by the subject, an amount of a composition comprising pterostilbene and nicotinamide; and
    all in an amount sufficient to reduce or reverse the gray in the hair.

2. The method of claim 1, wherein the composition further comprises vitamin A (retinol), and one or more retinoids.

3. The method of claim 1, wherein the composition further comprises one or more retinoids selected from at least one of retinyl palmitate, retinaldehyde, retinyl retinoate, retinyl proprionate, or tretinoin.

4. The method of claim 1, further comprising adding one or more pharmaceutically acceptable excipients.

5. The method of claim 1, wherein the composition comprises: 100 to 2,000 mg nicotinamide.

6. The method of claim 1, wherein the composition comprises: 50 to 1,000 mg pterostilbene.

7. The method of claim 1, wherein the composition comprises: 100 to 2,000 mg nicotinamide and 50 to 1,000 mg pterostilbene.

8. The method of claim 1, wherein the composition further comprises at least one of a chelating agent, a skin soothing agent, a skin conditioning agent, a humectant, a moisturizing agent, a nutrient, a thickener, or an emollient.

9. The method of claim 1, wherein the composition comprises per dose: 0.5 to 2 grams pterostilbene, and 1 to 5 grams nicotinamide, per 100 milliliters of water.

10. The method of claim 1, wherein the composition further comprises one or more excipients selected from water, Sodium Phytate, Aloe Barbadensis Leaf Juice, Glycerin, *Pyrus Malus* Fruit Extract, Phenoxyethanol, Ethylhexylglycerin, Tocopherol, Caprylic/Capric Triglyceride, *Argania Spinosa* Kernel Oil, Dipentaerythrityl Hexa C5-9 Acid Esters, Dimethicone, Acrylates/C10-30 Alkyl Acrylate Crosspolymer, Sodium Hydroxide, Hydroxyethyl Acrylate/ Sodium Acryloyldimethyl Taurate Copolymer, Squalane, Polysorbate 60, or Sorbitan Isostearate.

11. The method of claim 1, wherein the range per dose is 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300 mg of the composition per 100 ml of water.

12. The method of claim 1, wherein the range per dose is 150, 175, 200, 225, 250, 275, 300, 75 to 300, 80 to 275, 90 to 250, 100 to 225, 125 to 200, 150 to 175 mg of the composition per dose.

13. The method of claim 1, wherein the range per dose is 150, 175, 200, 225, 250, 275, 300, 325, 350, 375, 400, 425, 450, 475, 500, 525, 550, 575, 600, 50 to 600, 75 to 600, 80 to 575, 90 to 550, 100 to 525, 125 to 500, 150 to 475, 175 to 450, 200 to 425, 225 to 400, 250 to 375, 275 to 350, 300 to 325 mg per dose.

14. A method of reducing or reversing gray in hair in a subject in need thereof comprising:
 applying topically to and taking orally and nasally by the subject, an amount of a composition comprising pterostilbene and nicotinamide;
 wherein the composition comprises 0.5 to 2 grams pterostilbene and 1 to 5 grams nicotinamide per 100 milliliters of water when applied topically and nasally;
 wherein the composition comprises 50 to 1,000 mg pterostilbene and 100 to 2,000 grams nicotinamide when taken orally; and
 all in an amount sufficient to reduce or reverse the gray in the hair.

15. The method of claim 14, wherein the composition further comprises vitamin A, and one or more retinoids.

16. The method of claim 14, wherein the composition further comprises one or more retinoids selected from at least one of retinyl palmitate, retinaldehyde, retinyl retinoate, retinyl proprionate, or tretinoin.

17. The method of claim 14, wherein the composition further comprises one or more pharmaceutically acceptable excipients.

18. The method of claim 14, wherein the composition further comprises one or more excipients selected from water, Sodium Phytate, Aloe Barbadensis Leaf Juice, Glycerin, *Pyrus Malus* Fruit Extract, Phenoxyethanol, Ethylhexylglycerin, Tocopherol, Caprylic/Capric Triglyceride, *Argania Spinosa* Kernel Oil, Dipentaerythrityl Hexa C5-9 Acid Esters, Dimethicone, Acrylates/C10-30 Alkyl Acrylate Crosspolymer, Sodium Hydroxide, Hydroxyethyl Acrylate/ Sodium Acryloyldimethyl Taurate Copolymer, Squalane, Polysorbate 60, or Sorbitan Isostearate.

* * * * *